Patented Feb. 18, 1936

Plant Pat. 166

UNITED STATES PATENT OFFICE

166

PEACH

William C. Elliott, Modesto, Calif.

No Drawing. Application September 22, 1934, Serial No. 745,170

1 Claim. (Cl. 47—62)

My discovery relates to a new single variety of peach tree and to the fruit of the same.

My improved peach is a genuine freestone, the tree bearing the same originating from a bud sport planted in my orchard in 1923 in the Modesto district of Stanislaus County, California, and which tree was raised by me to maturity with the necessary care as to irrigation, cultivation, spraying etc. to insure the best crop results.

After picking the fruit upon the bearing of the tree I recognized the fruit as being a distinct and novel variety, having certain valuable characteristics not present in freestone peaches heretofore known, these being particularly the lateness of its ripening and the remarkable keeping qualities of the fruit after ripening and being picked.

As to the period of ripening of the fruit, this is some three weeks later than the Paloro variety (a cling peach to which my peach and its tree are very similar in appearance and size) and after the Elberta, Hale and other late varieties of freestone peaches are entirely off the market, but shortly before the Salwey variety matures.

It seems possible that the original peach tree from which my improved peach is produced is a cross between the Muir and Paloro varieties, since the fruit has the general appearance of the Paloro peach in color and texture of flesh, though ordinarily with a smaller amount of skin fuzz which is readily removed, while it has the characteristics of the Muir variety when subjected to a drying process.

The tree is of medium size, vigorous and upright, dense, hardy, very productive and a regular bearer. The trunk and branches are of medium size and medium between smooth and shaggy, the branches being brown in color. The lenticels are numerous and of medium size. The full sized leaves are large, averaging 6 inches in length and 1¾ inches in width. They are lanceolate in shape, acutely pointed, medium thin, smooth and dark green, with fine serrations along the edges. The petiole is long, and somewhat slender.

It will therefore be seen that the tree from which my new peach is obtained has the same general appearance, as to shape, size and other characteristics, as the Paloro, and it is as equally vigorous a tree.

The flower buds are hardy, of medium size and length, and are of plump appearance. The flowers are pink, of medium size, with about ten days between the first and full bloom, and have the same general appearance and time of blooming as the Paloro, Salwey, or other medium or late fruiting free stone peach.

For the above reasons I have deemed it unnecessary to accompany this application with a drawing since such drawing would not show any of the vital characteristics of my new peach and would appear but little if any different from any of the common varieties of freestone peaches, such as the Elberta and Salwey.

The trees begin to bear when about two years old, and the original tree since its first bearing year has had a heavy set each year, requiring a considerable thinning, and even then having an extremely large yield. Also, the fruit hangs well on the tree when mature and shows very little tendency to windfall.

The fruit is a perfect freestone of medium size, averaging approximately 2¾ inches in diameter in both directions so that it may be considered as practically spherical. Its suture is distinct but relatively shallow, extending from the base to slightly beyond the apex. The cavity is rounding, being elongated in the suture plane with the suture showing on both sides, and having a depth of about $\frac{3}{16}$ inch and a breadth at the base of about ¼ inch. The base is rounded, and the apex is short, with an apical pistil point. The stem averages ½ inch in length, is of medium size, and has medium adherence to the stone. The skin is of medium thickness and toughness, and somewhat tenacious to the flesh. The tendency to crack is very slight, and such tendency is not affected by a wet or dry season. The down or fuzz is of moderate amount, and quite short. Its surface color is mainly an evenly distributed orange yellow with a dash of crimson diffusing into the orange color from the stem end of the fruit. The depth of coloring of the peach however varies with the type of soil and fertilizing treatment given the tree in different years. The flesh is deep yellow in color, while the surface of the pit cavity is red. The juice is of moderate quantity and mediumly rich. The texture of the flesh is firm and fine, similar to that of the Paloro, but with few fibres. The fruit ripens evenly, has a sweet and mild flavor, but has no particular aroma. The stone is free, of medium size, with a length of about 1½″, a breadth of 1″, and a thickness of about ⅝″. It is of oval form, with an indented base, an acute apex, and is red in color, and has but slight tendency to split at any time.

The most valuable and novel characteristic of my improved peach however in addition to the lateness of its period of ripening is the remarkable keeping quality of the fruit after it matures. The peach can be picked ripe enough to eat and still be shipped or kept without any special attention and without refrigeration, for from ten to twenty-one days without deterioration, the flesh retaining its original firm texture and flavor for the duration of this period. It also requires no delicate handling for it to retain its good qualities, since this peach is not subject to easy bruising and the accompanying interior deterioration, as are other freestone peaches.

To test the keeping qualities of the fruit I actually shipped boxes of the same to eastern points some days after the fruit had been picked, without refrigeration, and ascertained that the fruit arrived at destination in perfect condition. I also placed a considerable quantity of the fruit, after picking the same ripe, in an open shed with no protection from the exterior late summer temperature ranging from 90° to 100°, and found the fruit in perfect condition after at least two weeks. As a matter of fact, the flavor of the peach and its juiciness improved for a week or more after picking. The flavor of my new peach is distinctive from other varieties and is very sweet and delicious. The peaches are good for drying and besides make excellent preserves as well as pies and the like, retaining their natural peachy flavor when cooked to a marked degree.

I claim:

The peach tree variety herein described, characterized by freestone fruit having texture similar to clingstone Paloro and the quality of keeping approximately fifteen days without refrigeration after being picked ripe.

WILLIAM C. ELLIOTT.